United States Patent [19]

Yamamoto

[11] Patent Number: 4,706,653
[45] Date of Patent: Nov. 17, 1987

[54] ENDOSCOPE DEVICE

[75] Inventor: Tsutomu Yamamoto, Hachioji, Japan

[73] Assignee: Olympus Optical Co., Ltd., Tokyo, Japan

[21] Appl. No.: 890,223

[22] Filed: Jul. 29, 1986

[30] Foreign Application Priority Data

Aug. 26, 1985 [JP] Japan .............................. 60-130693

[51] Int. Cl.⁴ .............................................. A61B 1/00
[52] U.S. Cl. ....................................................... 128/4
[58] Field of Search ......................................... 128/4, 6

[56] References Cited

U.S. PATENT DOCUMENTS

| 4,085,742 | 4/1978 | Okada | 128/4 |
| 4,219,013 | 8/1980 | Okada | 128/4 |
| 4,558,691 | 12/1985 | Okada | 128/6 |
| 4,660,982 | 4/1987 | Okada | 128/6 X |

Primary Examiner—William H. Grieb
Attorney, Agent, or Firm—Armstrong, Nikaido, Marmelstein & Kubovcik

[57] ABSTRACT

In this invention, an attachment for changing a view angle and visual field direction or protecting a tip portion and others is removably fitted to a tip portion of an endoscope inserting portion. A connecting member pulling in and fixing this attachment is rotatably and nonremovably fitted on the outer periphery of the tip portion of the endoscope inserting portion. In order that this connecting member may not be pulled out of the tip portion of the endoscope inserting portion, a groove is peripherally formed on the outer periphery of the tip portion and engaging members engaging in this groove and having an elastic deformability are provided on the connecting member.

4 Claims, 3 Drawing Figures

ENDOSCOPE DEVICE

BACKGROUND OF THE INVENTION

1. Field of the Invention

This invention relates to endoscope devices and more particularly to an endoscope device removably fitted in a tip portion of an endoscope inserting portion with an attachment for changing a view angle and visual field direction or protecting the tip portion and others.

2. Related Art Statement

There is recently extensively used a (medical) endoscope whereby an elongated inserting portion can be inserted into a body cavity to observe the interior of the body cavity or any treating tool can be used for such treatment as therapy. Among such endoscopes, there is also an industrial endoscope which can be inserted into an instrument or piping to inspect or treat its interior. Among such endoscopes, there are a flexible endoscope wherein the inserting portion is flexible and a rigid endoscope wherein the inserting portion is rigid.

Now, an endoscope is inserted, for example, into a body cavity, an illuminating light is radiated toward an object position within the body cavity, a reflected light from the object forms an image with an objective lens and the image is transmitted to an eyepiece through image guide fibers or the like so that the object can be sighted and observed. Therefore, depending on the object to be observed, it may be necessary to change a view angle or visual field direction and to protect the tip portion of the inserting portion or the object.

Therefore, there is already known a device which can be removably fitted in a tip portion of an endoscope inserting portion with an attachment for changing a view angle and visual field direction or protecting the tip portion. An example of it is shown in FIG. 1.

In FIG. 1, the reference numeral 1 represents an inserting portion of an endoscope and 2 represents a tip portion of the endoscope inserting portion. An attachment 3 for changing a view angle and visual field direction or protecting the tip portion 2 can be removably fitted to this tip portion 2. This attachment 3 has a recess 4 in which the endoscope tip portion 2 is to be engaged in the rear part, that is, on the endoscope connecting side and has a female screw 5 provided on the inner peripheral wall of the recess 4. On the other hand, a tubular connecting member 7 having a male screw 6 provided to be screwed with the above mentioned female screw 5 is rotatably fitted on the outer periphery of the endoscope tip portion. The male screw 6 of the connecting member 7 and the female screw 5 of the attachment 3 are screwed with each other and the connecting member 7 is rotated to pull in and fix the attachment 3 with the screws.

Now, in this formation, as a means whereby the tubular connecting member 7 removably fitted to the above mentioned endoscope tip portion 2 to fix the attachmnet 3 is held by the tip portion 2 so as not to be pulled off and dropped, conventionally a groove 8 in the peripheral direction has been peripherally formed in the tip portion of the connecting member 7 to be fitted on the outer periphery of the tip portion 2 and a C-ring 9 has been fitted in this groove 8.

However, in the connecting member holding means using the above mentioned conventional C-ring, in order that the C-ring may not be removed by an external force when the attachment is not fitted, it is necessary to elevate the dimensional precision of the C-ring. That is to say, the C-ring is in a form so plastically deformable that, when it is deformed, a space catching on the groove will be reduced and the C-ring will be likely to be removed. Therefore, it is necessary to take special care in working and storing the parts of the C-rings and assembling the products.

Such endoscope devices of this kind are seen to be suggested in the gazettes of Japanese utility model publications Nos. 31210/1984 and 87704/1982. In the prior art examples, a connecting member is rotatably and nonremovably fitted to the tip portion of an endoscope and a screw provided on the connecting member and a screw of the attachment are screwed with each other to screw and fix this attachment into the end portion of the endoscope. In these prior art examples, as a means whereby the connecting means for fixing the attachment to the endoscope tip portion is held in the endoscope tip portion so as not to be removable, the outer peripheral diameter of the endoscope tip portion in front of this connecting member is made larger or a flange is formed.

OBJECTS AND SUMMARY OF THE INVENTION

An object of this invention is to provide an endoscope device wherein a tubular member for removably fixing an attachment to a tip portion of an endoscope can be positively and rotatably locked in the endoscope tip portion and the parts can be easily made, stored, assembled and reduced.

Another object of this invention is to provide an endoscope device wherein the above mentioned connecting member can be easily fitted to the endoscope tip portion from the tip side and therefore the connecting member can be easily fitted.

Briefly, the endoscope device according to the present invention comprises an attachment having in the rear part a recess in which an inserting portion of an endoscope is engaged, having a female screw provided on the inner peripheral wall of the recess and removably connected and fixed to the tip portion, a connecting member rotatably fitted on the outer periphery of the tip portion of the inserting portion of the endoscope, having a male screw screwed with the female screw of the above mentioned attachment on the outer periphery on the tip side and pulling in and fixing the attachment, a groove formed peripherally on the outer periphery of the tip portion of the endoscope inserting portion in the tip side position of the connecting member and an engaging member extended to the tip portion of the connecting member and having an elastic deformability so as to be engaged with the above mentioned groove of the endoscope tip portion.

This and other objects and advantages of the present invention will become further apparent from the following detailed explanation.

BRIEF DESCRIPTION OF THE DRAWINGS

FIG. 2 is a sectioned view showing a tip portion of an endoscope.

FIG. 3 is a perspective view showing a connecting member.

BEST MODE FOR CARRYING OUT THE INVENTION

Figure 1:
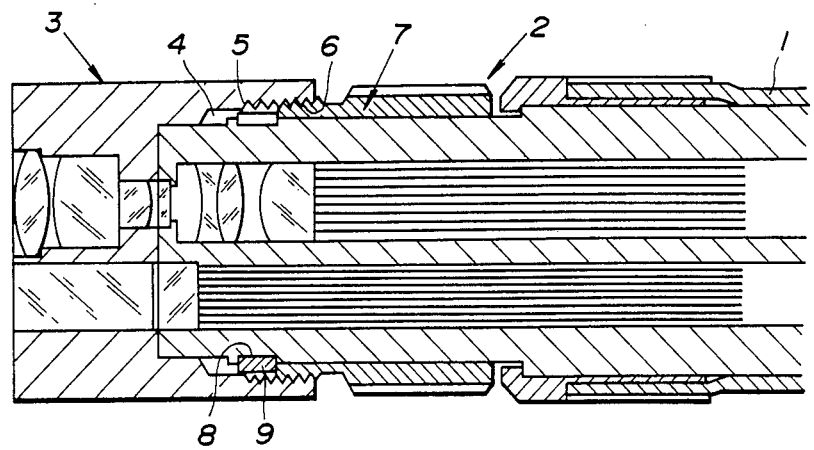
FIG. 1 is a sectional view showing a related art.
Figure 2:
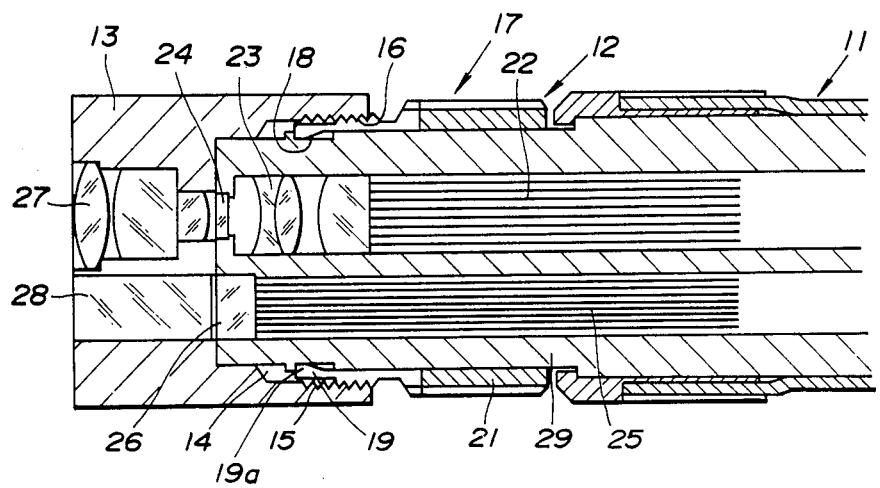
FIGS. 2 and 3 relate to an embodiment of the present invention.
Figure 3:
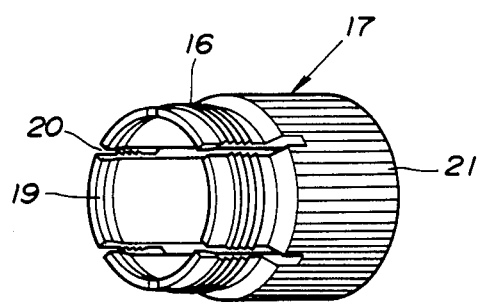

In FIGS. 2 and 3, the reference numeral 11 represents an inserting portion of an endoscope and 12 represents its tip portion. An attachment 13 for changing a view angle and visual field direction or protecting an objective lens and object so as not to be hurt can be removably connected and fixed to this tip portion 12. This attachment 13 has a recess 14 in which an endoscope tip forming portion 29 is to be engaged in the rear part, this is, on the endoscope connecting side and has a female screw 15 provided on the inner peripheral wall of the recess 14. On the other hand, a tubular connecting member 17 having a male screw 16 to be screwed with the female screw 15 of the above mentioned attachment 13 provided on the tip side is rotatably fitted on the outer periphery of the endoscope tip forming portion 29. Also, a groove 18 is peripherally formed on the outer periphery of the endoscope tip forming portion 29 in the tip portion position of this fitted connecting member 17.

The above mentioned connecting member 17 has an engaging member 19 having a projecting portion 19a projecting in the inside diameter direction so as to be engaged with the groove 18 in the position of the groove 18 when fitted to the tip portion, that is, to the endoscope and has a plurality of slits 20 formed thin in the axial direction so as to give the engaging member 19 an elastic deformability returning in a diameter contracting direction. The rear part side of this connecting member 17 is an operating portion 21 having knurls.

By the way, in the drawing, the reference numeral 22 represents image guiding fibers, 23 represents an objective lens, 24 represents a cover glass, 25 represents light guiding fibers, 26 represents a cover glass, 27 represents an objective system of the attachment and 28 represents an illuminating system.

In such formation, in assembling, when the tubular connecting member 17 is fitted to the endoscope tip forming portion 29 from the tip side and the engaging member 19 of the connecting member 17 passes over the edge part of the groove 18, it will be elastically deformed in a diameter expanding direction but, on the other hand, when the engaging member 19 passes over the edge part of the groove 18 and comes to the groove 18, the engaging member 19 will return to the original diameter and will be engaged with the groove 18 and the connecting member 17 will be able to be rotatably and positively locked in the endoscope tip forming portion 29. Therefore, once the above mentioned connecting member 17 is fitted to the endoscope tip forming portion 29, even if an ordinarily expected external force is applied, the tip side having the engaging member 19 will be very unlikely to be expanded and, even if one side of the tip side divided by the slits 20 is expanded, unless the remaining tip side is simultaneously expanded, the engaging member 19 will not be disengaged with the groove 18. Also, this connecting member is more rigid in the structure than the C-ring and requires no working dimensional precision and the stock of the parts is easy to control. Further, in assembling, if the connecting member 17 is only pushed onto the outer periphery of the endoscope tip forming portion, the connecting member 17 will be assembled and therefore will be high in the workability.

By the way, in this invention, the groove 18 formed peripherally on the outer periphery of the tip forming portion 29 may be formed by providing a peripheral projection or being cut to be of a small diameter without providing a projection.

In this invention, it is apparent that working modes different in a wide range can be formed on the basis of this invention without departing from the spirit and scope of the invention. This invention is not restricted by any specific embodiment except being limited by the appended claims.

What is claimed is:

1. An endoscope device removably fitted with an attachment in a tip portion of an endoscope inserting portion, characterized by comprising:

an attachment having in the rear part a recess in which the tip portion of an endoscope inserting portion is engaged, having a female screw provided on the inner peripheral wall of this recess and removably connected and fixed to the tip portion of the endoscope inserting portion;

a connecting member rotatably and nonremovably fitted to the outer periphery of the tip portion of the endoscope inserting portion, having on the outer periphery a male screw screwed with the female screw of the attachment and pulling in and fixing the attachment;

a groove which is peripherally formed on the outer periphery of the tip portion of the endoscope inserting portion and in which the tip side of this connecting member will be positioned when the connecting member is fitted; and a plurality of engaging members provided to extend on the tip side of the connecting member, having an elastic deformability returning in a diameter contracting direction and engaged in the peripheral groove formed on the outer periphery of the tip portion of the endoscope inserting portion to prevent the connecting portion from being pulled out.

2. An endoscope device according to claim 1 wherein said connecting member is formed to be tubular.

3. An endoscope device according to claim 1 wherein said engaging members provided to extend in the tip of the connecting member are given an elastic deformability returning in a diameter contracting direction by a plurality of slits formed in the axial direction.

4. An endoscope device according to claim 1 wherein said connecting member has finger catching parts formed on the outer periphery in the rear of the male screw part.

* * * * *